US00PP37466P2

(12) United States Plant Patent
Carrella

(10) Patent No.: US PP37,466 P2
(45) Date of Patent: Jun. 9, 2026

(54) ***CALIBRACHOA* PLANT NAMED 'KLECA24A54'**

(50) Latin Name: ***Calibrachoa* sp.**
Varietal Denomination: KLECA24A54

(71) Applicant: KLEMM + SOHN GMBH & CO. KG, Stuttgart (DE)

(72) Inventor: Angelo Carrella, Palma Campania (IT)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/294,272

(22) Filed: Aug. 7, 2025

(51) Int. Cl.
*A01H 5/02* (2018.01)
*A01H 6/82* (2018.01)

(52) U.S. Cl.
USPC ..... Plt./413

(58) Field of Classification Search
USPC ..... Plt./413
See application file for complete search history.

(56) References Cited

U.S. PATENT DOCUMENTS

PP19,863 P2 * 3/2009 Pierce ..... A01H 6/821 Plt./413

OTHER PUBLICATIONS https://info.ballseed.com/PlantInfo/?phid=066007160039408 (retrieved online Sep. 16, 2025) (Year: 2025).*

* cited by examiner

*Primary Examiner* — Susan Mccormick Ewoldt
*Assistant Examiner* — Zachariah Allan Kay
(74) *Attorney, Agent, or Firm* — Weatherly IP Solutions, LLC; James M. Weatherly

(57) ABSTRACT

A new *Calibrachoa* plant particularly distinguished by having pink flowers with pink-red centers and a semi-trailing plant habit, is disclosed.

1 Drawing Sheet

Genus and species: *Calibrachoa* sp.
Variety denomination: 'KLECA24A54'.

BACKGROUND OF THE NEW PLANT

The present invention comprises a new and distinct variety of *Calibrachoa*, botanically known as *Calibrachoa* sp., and hereinafter referred to by the variety name 'KLECA24A54'. 'KLECA24A54' originated during May 2020 in Nairobi, Kenya from a controlled-cross between the female *Calibrachoa* variety 'KLECA22901' (unpatented) and the male *Calibrachoa* variety 'KLECA20803' (U.S. Plant Pat. No. 33,988).

Seeds from the controlled cross were sown, cultivated into adult plants and evaluated. A single plant was selected during May 2021 in Stuttgart, Germany and designated 'KLECA24A54'. 'KLECA24A54' was vegetatively propagated by cuttings and found to reproduce true to type in successive generations of asexual propagation.

SUMMARY

The following are the most outstanding and distinguishing characteristics of this new variety when grown under normal horticultural practices in Stuttgart, Germany.

1. Pink flowers with pink-red centers; and
2. Semi-trailing plant habit.

DESCRIPTION OF THE PHOTOGRAPH

This new *Calibrachoa* plant is illustrated by the accompanying photograph taken in May 2024 which shows an overall view the whole plant. The 11-week-old-plant was grown indoors in Stuttgart, Germany. The colors shown are as true as can be reasonably obtained by conventional photographic procedures.

DESCRIPTION OF THE NEW VARIETY

The following detailed descriptions set forth the distinctive characteristics of 'KLECA24A54'. The data which define these characteristics were collected from asexual reproductions carried out in Latina, Italy. Data was collected on 14-week old plants after transplant in Latina, Italy. Color references are to The R.H.S. Colour Chart of The Royal Horticultural Society of London (R.H.S.), 5$^{th}$ edition (2007).

Classification:
*Family.*—Solanaceae.
*Species.*—*Calibrachoa* sp.
*Common name.*—*Calibrachoa.*

Parentage:
*Female.*—'KLECA22901' (unpatented).
*Male.*—'KLECA20803' (U.S. Plant Pat. No. 33,988).

Plant description:
*Life cycle.*—Annual.
*Form.*—Short-lived subshrub.
*Habit.*—Semi-trailing.
*Height (from soil line to top of foliage).*—11.1 cm.
*Spread.*—58.3 cm.

Propagation:
*Type cuttings.*—Tip cutting.
*Time to produce a rooted cutting.*—3 weeks.

Stems:
*Stem color.*—145B.

*Pubescence color.*—155A.
*Stem diameter.*—0.1 cm.
*Stem length.*—From soil line to first node: 0.9 cm. Total length: 31.2 cm.
*Internode length.*—2.1 cm.

Leaves:
*Arrangement.*—Alternate.
*Shape.*—Cuneate.
*Apex.*—Obtuse.
*Base.*—Acute.
*Margin.*—Ciliate.
*Pubescence color.*—155A.
*Venation color.*—Upper surface: 137B. Lower surface: 138B.
*Length.*—3.1 cm (mature leaves).
*Width.*—1.2 cm (mature leaves).
*Color.*—Upper surface: 137B. Lower surface: 138B.
*Fragrance.*—Absent.

Flowers:
*Flowering habit.*—Single flower.
*Flower type.*—Single.
*Duration of flowers.*—7 to 12 days.
*Corolla.*—Smooth.
*Shape.*—Funnel form.
*Fragrance.*—Absent.

Flower buds:
*Surface.*—Pubescent.
*Length.*—2.2 cm.
*Diameter.*—0.4 cm.
*Shape.*—Irregular to oblong.
*Color.*—67D (top buds), 150D (base buds).

Peduncle:
*Length.*—1.5 cm.
*Diameter.*—Less than 0.1 cm.
*Color.*—144C.
*Texture.*—Pubescent.
*Anthocyanin.*—Absent.

Flower description:
*Flower depth.*—2.1 cm.
*Flower tube length.*—1.6 cm.
*Flower tube diameter.*—0.5 cm.
*Flower diameter.*—3.8 cm.
*Pedicel color.*—144B.

Sepals:
*Shape.*—Ovate.
*Apex.*—Narrow acute.
*Margin.*—Ciliate.
*Length.*—0.9 cm.
*Diameter.* 0.3 cm.
*Sepal color.*—Upper surface: 143A. Lower surface: 143B.

Petals:
*Shape.*—Truncated.
*Length.*—1.6 cm.
*Apex.*—Obtuse.
*Margin.*—Entire.
*Base.*—Fuse in the tube.
*Pubescence.*—Absent.
*Lobe length.*—1.6 cm.
*Lobe width.*—1.5 cm.
*Lobe color.*—Upper surface: 51C main color and 46B center pattern. Lower surface: 39C main color.
*Corolla tube color.*—Inner: 12C. Outer: 4C.
*Fragrance.*—Absent.

Reproductive organs:
*Stamen number.*—5.
*Stamen color.*—Anther color: 13B. Filament color: 1C. Pollen color: 12A.
*Placenta arrangement.*—Ovate.
*Pistil number.*—1.
*Pistil length.*—0.7 cm.
*Stigma color.*—145B.
*Style length.*—0.6 cm.
*Style color.*—145B.

Fruit/seed set: None observed.

Disease/insect resistance: No pests and disease were observed.

COMPARISON WITH PARENTAL LINES AND KNOWN VARIETY

'KLECA24A54' is distinguished from its parents as described in Table 1:

TABLE 1

Comparison with Parental Lines

| Trait | Variety 'KLECA24A54' | Female parent | Male Parent |
|---|---|---|---|
| Flower color | Pink with pink-red center | White | Yellow |
| Habit | Semi-trailing | Trailing | Mounding |

'KLECA24A54' is most similar to the *Calibrachoa* plant named 'KLECA24A17' (unpatented). Differences between the two varieties are described in Table 2:

TABLE 2

Comparison with Similar Variety

| Trait | Variety 'KLECA24A54' | Commercial line 'KLECA24A17' (unpatented) |
|---|---|---|
| Flower color | Pink with pink-red center | Light blue with dark blue center |

I claim:

1. A new and distinct variety of *Calibrachoa* plant named 'KLECA24A54' as shown and described herein.

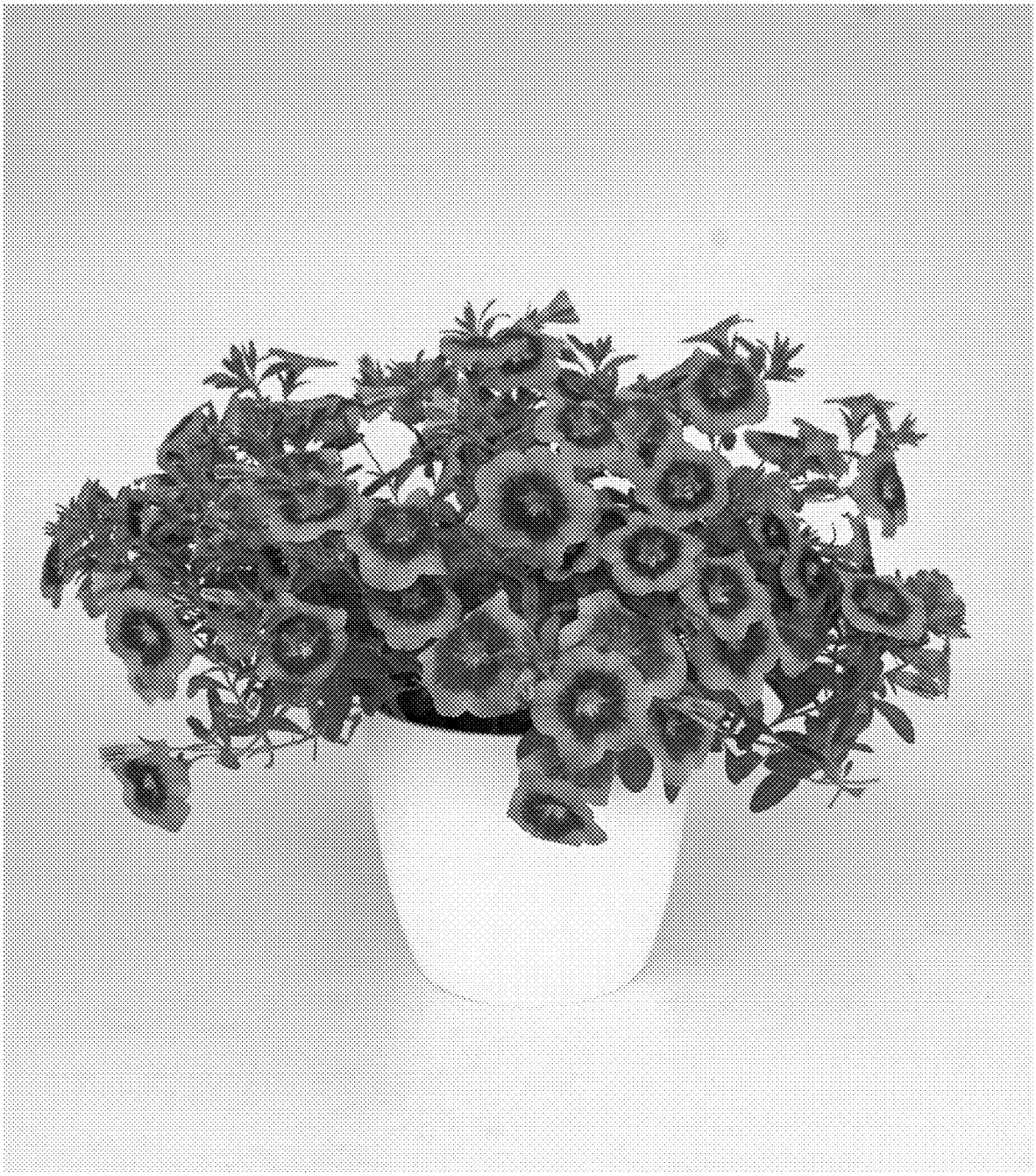

* * * * *